United States Patent
Liu et al.

(12)

(10) Patent No.: US 10,759,737 B2
(45) Date of Patent: Sep. 1, 2020

(54) METHOD FOR EXTRACTING 1,5-PENTANEDIAMINE FROM SOLUTION SYSTEM CONTAINING 1,5-PENTANEDIAMINE SALT

(71) Applicants: Cathay Biotech Inc., Shanghai (CN); CIBT America Inc., Newark, DE (US)

(72) Inventors: Xiucai Liu, Shanghai (CN); Bingbing Qin, Shanghai (CN); Chen Yang, Shanghai (CN)

(73) Assignees: CATHAY BIOTECH INC., Shanghai (CN); CIBT AMERICA INC., Newark, DE (US)

( * ) Notice: Subject to any disclaimer, the term of this patent is extended or adjusted under 35 U.S.C. 154(b) by 0 days.

(21) Appl. No.: 16/075,929

(22) PCT Filed: Sep. 7, 2016

(86) PCT No.: PCT/CN2016/098303
§ 371 (c)(1),
(2) Date: Aug. 6, 2018

(87) PCT Pub. No.: WO2017/133242
PCT Pub. Date: Aug. 10, 2017

(65) Prior Publication Data
US 2019/0055186 A1 Feb. 21, 2019

(30) Foreign Application Priority Data
Feb. 6, 2016 (CN) .......................... 2016 1 0083713

(51) Int. Cl.
| | |
|---|---|
| *C07C 209/86* | (2006.01) |
| *C12P 13/00* | (2006.01) |
| *C07C 211/09* | (2006.01) |
| *C07C 209/84* | (2006.01) |
| *B01D 3/10* | (2006.01) |
| *B01D 11/04* | (2006.01) |

(52) U.S. Cl.
CPC .............. *C07C 209/86* (2013.01); *B01D 3/10* (2013.01); *B01D 11/0492* (2013.01); *C07C 209/84* (2013.01); *C07C 211/09* (2013.01); *C12P 13/00* (2013.01)

(58) Field of Classification Search
CPC ..... B01D 11/0492; B01D 3/10; C07C 209/84; C07C 209/86; C07C 211/09; C12P 13/00
See application file for complete search history.

(56) References Cited

U.S. PATENT DOCUMENTS

| | | | |
|---|---|---|---|
| 7,977,514 B2 | 7/2011 | Peters et al. | |
| 8,906,653 B2 * | 12/2014 | Volkert | C07C 209/84 |
| | | | 210/601 |
| 9,617,202 B2 | 4/2017 | Hiura et al. | |
| 9,914,694 B2 * | 3/2018 | Liu | C07C 209/84 |
| 2011/0004018 A1 * | 1/2011 | Ito | B01D 61/027 |
| | | | 564/138 |

FOREIGN PATENT DOCUMENTS

| | | |
|---|---|---|
| CN | 101356151 A | 1/2009 |
| CN | 101970393 A | 2/2011 |
| CN | 101981202 A | 2/2011 |
| CN | 102056889 A | 5/2011 |
| CN | 102782146 A | 11/2012 |
| CN | 204400884 U | 6/2015 |
| CN | 104762336 A | 7/2015 |
| CN | 104974046 A | 10/2015 |
| EP | 2263996 A1 | 12/2010 |
| EP | 2975020 A1 | 1/2016 |
| JP | 2008193898 A | 8/2008 |
| JP | 2009096796 A | 5/2009 |
| JP | 2009131239 A | 6/2009 |
| WO | 2007079944 A1 | 7/2007 |
| WO | 2014113999 A1 | 7/2014 |
| WO | 2015025896 A1 | 2/2015 |
| WO | 2015076238 A1 | 5/2015 |
| WO | 2017/079872 A1 | 5/2017 |

OTHER PUBLICATIONS

Gong Tingyun, "Recent advances in the production and application of 1,5-diaminopentane", Jurnal of Chemical Industry & Engineering, vol. 34 No. 1, Feb. 2013, pp. 55-58.

* cited by examiner

*Primary Examiner* — Sudhakar Katakam
*Assistant Examiner* — Jennifer C Sawyer
(74) *Attorney, Agent, or Firm* — Fox Rothschild LLP

(57) ABSTRACT

Provided is a method for extracting a 1,5-pentanediamine from a solution system containing a 1,5-pentanediamine salt. The method comprises adding to the solution system an insoluble basic substance to form a solution system containing free 1,5-pentanediamine. The provided method has high applicability, is easy to use, and is environmentally-friendly, significantly lowering raw material costs and operating costs for the entire manufacturing process. The method achieves a high recovery rate for pentanediamine, and is more suitable for industrial-scale production.

13 Claims, No Drawings

METHOD FOR EXTRACTING 1,5-PENTANEDIAMINE FROM SOLUTION SYSTEM CONTAINING 1,5-PENTANEDIAMINE SALT

TECHNICAL FIELD

The invention relates to the field of separation and purification of chemical products, in particular to a method for extracting 1,5-pentanediamine from solution system containing 1,5-pentanediamine salt.

BACKGROUND ART

Pentanediamine (i.e., 1,5-pentanediamine, 1,5-diaminopentane, cadaverine) is an important polymeric monomer. Starting from 1,5-pentanediamine, a series of polyamides, such as polyamide 56, polyamide 510, or polyester amides can be synthesized, and is widely used in textiles, electronic appliances, mechanical equipment, automobiles and other fields.

The patents related to the production and purification of 1,5-pentanediamine are cited as follows:

In CN101981202A, pentanediamine is produced directly from fermentation, where a fermentation broth is refluxed at 103° C. for 5 hours to cleave the by-products contained therein, which is then subjected to multiple extractions with butanol, and evaporation of the organic solvent to obtain a pentanediamine product. In the process of extracting pentanediamine with an organic solvent, due to the characteristics of pentanediamine, polar organic solvents are usually used for the extraction. In such a process, organic solvents such as chloroform or butanol are used. During extraction, solvent is inevitably volatilized, causing environmental pollution, and thus a subsequent solvent recovery step must be performed, which increases the extraction cost.

In CN200980121108, the enzyme solution of pentanediamine is treated with an organic membrane of UF12000 molecular weight to reduce the trifunctional organic matter in the reaction solution. The treated pentanediamine solution is heated to above 100° C. to decompose pentanediamine carbonate, followed by distillation of pentanediamine to obtain the product. Decomposition of carbonate requires a relatively high temperature and long-time heating, whereas a complete decomposition of carbonate is not guaranteed, which has an adverse affect on the distillation process and product quality. This method is only suitable for the separation of 1,5-pentanediamine from pentanediamine carbonate, and thus its suitability is very limited.

CN 101970393A discloses a process comprising a step of adding an alkaline solution and subjecting the solution to nanofiltration instead of extraction to increase the recovery rate of pentanediamine. However, nanofiltration is not suitable for the case where a large amount of solid impurities is present. When the system contains a large amount of solid impurities such as bacteria or precipitates of inorganic salts or macromolecular impurities, if nanofiltration is used, prefiltration by microfiltration or even ultrafiltration must be carried out prior to nanofiltration. Otherwise, the nanofiltration flux is low and the membrane is easily blocked, which consumes time and energy and reduces the service life of the nanofiltration membrane. Moreover, the method is basically applicable only to the case where a soluble alkali or alkali solution is added. If the pentanediamine salt is replaced with sodium hydroxide or potassium hydroxide, a large amount of salts such as sodium sulfate, sodium chloride or potassium sulfate is present in the final solution system, and precipitation in the later distillation may affect the evaporation yield of pentanediamine.

DISCLOSURE OF THE INVENTION

In order to overcome such defects as too complicated process, high cost, and low recovery rate of separation in the process of purifying and separating pentanediamine in the prior art, the present invention is aimed to provide a method of extracting 1,5-pentanediamine from a solution system containing 1,5-pentanediamine salt.

The present invention provides an extraction method by adding a basic substance to a solution system to form a solution system containing free 1,5-pentanediamine; wherein the 1,5-pentanediamine salt comprises at least one or more of sulfate, carbonate, phosphate of 1,5-pentanediamine; said basic substance comprises at least one or more of solid calcium hydroxide, magnesium hydroxide, calcium oxide, and magnesium oxide.

In the method provided by the invention, the molar amount of sulfate, carbonate and phosphate of 1,5-pentanediamine in the solution system is not less than 70%, preferably not less than 75%, more preferably not less than 80%, further preferably not less than 85%, and most preferably not less than 90% of the total molar amount of 1,5-pentanediamine salt in the solution system.

In the method provided by the invention, the solution system containing 1,5-pentanediamine salt further comprises hydrochloride and/or dicarboxylate of 1,5-pentanediamine.

In the method provided by the present invention, the basic substance further comprises one or more of sodium hydroxide, potassium hydroxide and ammonia.

In the method provided by the present invention, the solution system containing 1,5-pentanediamine salt is an aqueous solution containing 1,5-pentanediamine salt, an enzyme converting solution of 1,5-pentanediamine or a fermentation broth of 1,5-pentanediamine.

In the method provided by the present invention, the temperature at which the basic substance is added is not particularly limited, but the reaction would be accelerated as the temperature increases. Preferably, the reaction temperature after the addition of base is from room temperature to 95° C., more preferably, above 60° C.

The method provided by the present invention further comprises subjecting the obtained solution system containing free 1,5-pentanediamine to distillation/evaporation to obtain a 1,5-pentanediamine solution.

In the method provided by the present invention, the method further comprises separating solid substances after forming a solution system containing free 1,5-pentanediamine.

In the method provided by the present invention, the obtained solution system containing free 1,5-pentanediamine is concentrated prior to distillation/evaporation.

In the method provided by the present invention, for the distillation/evaporation, the temperature is 40 to 250° C. and the pressure is not greater than −0.05 MPa.

The method provided by the present invention further comprises a pretreatment process for sterilization and/or decolorization and/or concentration prior to the addition of the basic substance.

In the current separation and extraction technology of pentanediamine, addition of strong bases such as sodium hydroxide solution to replace the pentanediamine salt with free pentanediamine, and soluble inorganic salt is generally conceived, and when a weak base or a poorly soluble base is used, it is considered that due to the relatively strong basicity of pentanediamine, it is difficult to achieve a complete reaction of pentanediamine salt by adding a weak base or a poorly soluble base. Solid impurities remaining in the system and the produced hardly soluble inorganic salt precipitates may affect the yield of pentanediamine. Under such a technical concept, in the prior art, when a base is to be added, a dilute solution added with a soluble base such as sodium hydroxide, potassium hydroxide or a poorly soluble base is used in order to avoid solid formation during the conversion of the pentanediamine salt, or the solid-liquid separation process is strengthened after the reaction of adding base to avoid the influence of solid precipitation on distillation/evaporation, and to improve the recovery of pentanediamine. However, the inventors have found through a large number of experiments that purification of pentanediamine using a weak base or a poorly soluble base or a basic substance such as calcium oxide, calcium hydroxide, magnesium hydroxide or the like under specific conditions can also obtain the desirable yield and extraction rate. Even in case where solid impurities such as bacteria or solid inorganic salt precipitates are present in the solution system, the extraction method of the present invention is still effective, and finally pentanediamine can be obtained with a desirable yield.

The extraction method of the present invention is used for sulfate, phosphate, carbonate, and the like of pentanediamine, and is different from the prior art in that a poorly soluble base such as calcium oxide, calcium hydroxide, magnesium hydroxide or the like is added for the formation of poorly soluble inorganic salt precipitates in the solution system. Formation of the precipitates promotes the continuous dissolution process of the above-mentioned poorly soluble base in the solution, thereby continuously and stably converting the pentanediamine salt to pentanediamine, which greatly increases the conversion rate of pentanediamine. The invention overturns the conventional belief that poorly soluble substance is not sufficiently reacted in the solution or that weak base cannot prepare strong base, and obtains an unexpected technical effect. Moreover, poorly soluble bases such as calcium oxide and calcium hydroxide are more cost-competitive than commonly used strong bases such as sodium hydroxide, especially in industrial applications, where poorly soluble bases are directly fed in solid form, which facilitates more to storage, plant operation and transportation.

The extraction method of the present invention further comprises a step of distillation/evaporation to obtain a solution containing free pentanediamine. When the basic substance is a strong base such as sodium hydroxide, although the salts thus formed are soluble in the solution system, inorganic salts gradually precipitate as water is distilled out during distillation/evaporation. If the solution system also contains impurities such as bacteria, proteins, polysaccharides, organic pigments, a viscous bottom liquid of distillation/evaporation may even be formed, which will affect the stirring as well as the heat and mass transfer efficiency. Pentanediamine entrapped in the bottom liquid of distillation/evaporation cannot be distillated out, which results in the final relatively low distillation/evaporation yield, and the distillation/evaporation waste is also very difficult to be handled, which greatly increases the manufacturing costs and environmental stress in the industry. The extraction method of the invention forms solid inorganic salt precipitates prior to distillation/evaporation, which can be conveniently removed by filtration, centrifugation, and that large amount of inorganic salt precipitates would not be present in the subsequent distillation/evaporation process, which makes the distillation/evaporation process easier to be carried out. Further, the inventors have also found that, by using the method of the present invention, even the presence of solid inorganic salts does not affect the distillation/evaporation process, distillation/evaporation can be directly carried out without solid-liquid separation after the addition of the poorly soluble base. The inorganic salt solids which is instrically present and the unreacted base can disperse the organic impurities in the solution, making it less prone to agglomeration, thereby increasing the evaporation efficiency and the final yield of pentanediamine.

In addition, as compared with conventional extraction methods, another significant advantage of the present invention is that the amount of water-soluble inorganic salt in the wastewater is significantly reduced, and the difficulty of wastewater treatment is alleviated. In the current circumstances where the environmental protection requirements are gradually increased, the distillation/evaporation waste from the method of the present invention is easier for carrying out the three-waste treatment, which can significantly reduce cost and environmental pressure.

The extraction method provided by the invention has the advantages of high practicability, simple process and simple operation, and can significantly reduce the raw material cost and operational cost of the entire process. The method of the invention has a high recovery rate of pentanediamine, and the recovered pentanediamine solution has a good purity, and can be directly used, or the high purity grade pentanediamine product can be obtained by simple treatment. In summary, the method of the invention is simple in process, low in cost, environmentally friendly, and more suitable for industrial production.

DETAILED DESCRIPTION OF THE EMBODIMENTS

The invention provides a method for extracting 1,5-pentanediamine from a solution system containing 1,5-pentanediamine salt, which comprises: adding to the solution system a basic substance to form a solution system containing free 1,5-pentanediamine, wherein the 1,5-pentanediamine salt comprises at least one or more of sulfate, carbonate, and phosphate of 1,5-pentanediamine. The basic substance comprises at least one or more of solid calcium hydroxide, magnesium hydroxide, calcium oxide, magnesium oxide, which react with one or more of the sulfate, carbonate, phosphate of 1,5-pentanediamine.

In one embodiment of the method according to the present invention, the molar amount of sulfate, carbonate, and phosphate of 1,5-pentanediamine in the solution system is not less than 70%, preferably not less than 75%, more preferably not less than 80%, further preferably not less than 85%, and most preferably not less than 90% of the total molar amount of 1,5-pentanediamine salt in the solution system.

At present, the industrial preparation of 1,5-pentanediamine is mostly carried out by a biological method. Therefore, in one embodiment of the method according to the present invention, the solution system containing 1,5-pentanediamine salt can be a fermentation broth containing 1,5-pentanediamine salt produced by biological fermentation, or an enzyme converting solution, or an enzyme converting solution of pentanediamine salt obtained by reaction of a lysine salt under the action of lysine decarboxylase (LDC), or may also be an aqueous solution containing 1,5-pentanediamine salt. Industrially available pentanediamine salt solutions are generally obtained by fermentation or enzymatic conversion processes. At the end of fermentation or enzymatic conversion, the pH of the aqueous solution is generally near neutral, and the pentanediamine is present in salt form in the aqueous solution. The enzyme converting solution or fermentation broth according to the present invention may be a stock solution containing bacteria without having subjected to any treatments. The fermentation broth or the enzyme converting solution is not particularly limited in the present invention. One of the technical effects of the present invention is that a fermentation/enzyme converting stock solution containing a large amount of soluble/insoluble impurities can be processed, and pre-separation steps such as sterilization and removal of impurity in the prior art process can be omitted, but the solution containing 1,5-pentanediamine is not limited to a fermentation/enzyme converting stock solution only. It can be inferred that the 1,5-pentanediamine solution system containing no/part of soluble/insoluble impurities does not affect the effect of the present invention. Therefore, the solution system containing 1,5-pentanediamine may also be a solution system obtained after further treatment (collectively referred to as a treatment liquid), such as a clear solution obtained by filtering macromolecular substances such as bacteria or proteins through a ceramic membrane or an ultrafiltration membrane, or a solution obtained by simple filtration, or the supernatant obtained by centrifugation, or a solution obtained by decolorization and impurity removal technology using an activated carbon, or an aqueous solution of pentanediamine formed by dissolving pentanediamine in water. In these processes, insoluble impurities or soluble impurities can be removed, and 1,5-pentanediamine salt can be retained in the solution system. Further, the enzyme converting solution or the fermentation broth, or the treatment liquid from the above-mentioned treatments may be further concentrated, and concentration may be carried out by any applicable methods in the prior art such as evaporation, atmospheric distillation, vacuum distillation, reverse osmosis. That is, the solution system containing 1,5-pentanediamine salt is a mixed system of an aqueous solution of inorganic salts or organic salts containing 1,5-pentanediamine, and may be a pure solution system, or may comprise solid microorganisms or compound impurities, which do not affect the extraction method of the present invention.

Specifically, the solution system containing 1,5-pentanediamine salt according to the present invention refers to a pentanediamine salt solution obtained by reacting a lysine salt solution under the action of lysine decarboxylase (LDC), or to a solution of pentanediamine salt obtained by direct fermentation. The specific method for preparing pentanediamine using enzyme converting solution of pentanediamine salt or via direct fermentation is not particularly limited, and those skilled in the art can determine the specific raw materials and process parameters for the specific enzyme converting process according to the prior art, thereby a solution system containing 1,5-pentanediamine salt is obtained.

The lysine salt for the production of pentanediamine by enzyme conversion may be a solution of lysine salt formed by dissolving an inorganic salt or an organic salt of lysine, such as commercially available lysine hydrochloride, lysine sulfate in water. Another example is a lysine salt solution formed by dissolving lysine hydrochloride produced by biological fermentation, a lysine sulfate product or a fermentation broth in water. In the industrial large-scale production of lysine by fermentation, ammonium sulfate is used as one of the nitrogen sources in the medium, so the fermentation broth contains a large amount of sulfate, and the fermentation broth can also be used as a lysine salt solution. The lysine fermentation broth may directly use fermentation stock solution, or may be a fermentation broth obtained by having it pretreated to remove the impurities from the fermentation broth, such as a fermentation supernatant obtained by having the fermentation broth subjected to treatments like centrifugation, filtration, or membrane filtration to remove the bacteria, or a decolored lysine salt solution obtained by adding activated carbon to the lysine fermentation broth for decolorization, and then filtering.

The above lysine decarboxylase refers to an enzyme capable of acting on lysine or a salt to form 1,5-pentanediamine. The lysine decarboxylase may be a fermentation broth of lysine decarboxylase, or a decarboxylase cell obtained by centrifugation or filtration or other technical means, or a broken cell, or a supernatant of fermentation broth solution obtained by filtering the cell, or refined enzymes. It may also be a mixture of two or more enzymes. The microorganism producing the lysine decarboxylase may be a wild strain, a mutagenized strain, or a genetically recombined strain.

The process for decarboxylation of lysine in the present invention is not particularly limited, and any existing enzyme conversion techniques may be employed, or a simple improvement can be made by those skilled in the art in the prior art.

For example, Zhu Xi ("Microbial transformation of L-lysine for cadaverine research", master thesis, Tianjin University of Science and Technology, March 2009) proposed the following four methods:

(1) Direct reaction: The lysine hydrochloride was directly added to the lysine decarboxylase fermentation broth until a substrate concentration of 0.05 mol/kg was obtained, and the reaction was carried out for 2 hours, and the molar conversion rate was 36.05%.

(2) Buffer system enzymatic reaction: The pH of the reaction system was buffered with 0.6 N acetic acid buffer. The final concentration of lysine hydrochloride in the buffer solution was 0.22 mol/kg, the reaction was carried out for 2 h, and the molar conversion rate was 81.30%.

(3) pH-controlled enzymatic reaction: strong acid control reaction pH 5-6, the concentration of lysine hydrochloride in the enzymatic reaction system was 0.22 mol/kg, the reaction was carried out for 2 h, and the molar conversion rate was 94.97%.

(4) pH-controlled batch enzymatic reaction: strong acid control reaction pH 5-6, the initial lysine hydrochloride concentration in the reaction system was 0.22 mol/kg, and the product and enzyme were separated in situ for a certain period of time, the final conversion substrate was 0.87 mol/kg. The cadaverine yield was 94.61%.

For example, Chinese Patent No. CN 102782146A discloses that the microorganisms expressing lysine decarboxylase are subjected to a freeze-thaw treatment, a heat treatment, a lysine salt treatment prior to the enzyme conversion to improve the efficiency. Japanese Patent Publication JP20050147171 discloses enzymatic catalysis using a lysine carbonate aqueous solution as a substrate and adjusting the pH with carbon dioxide.

For example, Chinese Patent application ZL 201410004636.3 discloses the preparation of 1,5-pentanediamine by decarboxylation of a lysine fermentation broth.

In the lysine decarboxylation reaction, other components such as inorganic salts, vitamins, or any other additives which contribute to the enzymatic reaction process may be additionally added as needed.

In the lysine decarboxylation reaction, the reaction temperature is usually 20° C. or more and 60° C. or less.

The fermentation broth of pentanediamine salt of the present invention refers to a fermentation broth containing pentanediamine salt obtained by up-regulating the expression of lysine decarboxylase in a strain capable of producing lysine by genetic technology, or by recombinantly expressing lysine decarboxylase to simultaneously convert lysine into pentanediamine in a fermentation process. The recombined bacteria are not particularly limited in the present invention, provided that pentanediamine is obtained. For example, "one-step production of genetically engineered bacteria of 1,5-pentanediamine glutamic acid *Corynebacterium*" (Niu Tao et al., Chinese Journal of Bioengineering, 2010, 30(8): 93-99) discloses the use of the *Hafnia alvei* genome as the template, and the lysine decarboxylase gene ldc is obtained via PCR amplification, and the *Escherichia coli/Corynebacterium glutamicum* shuttle plasmid is used as a vector. The target gene fragment obtained from amplification was cloned into *Corynebacterium glutamicum*, and the recombinant strain was obtained. As another example, PCT/CN2015/094121 discloses a process for the direct production of 1,5-pentanediamine by fermentation. Those skilled in the art know how to optimize the composition, ratio and fermentation process parameters of the medium according to the particular recombinant bacteria. A fermentation broth of pentanediamine salt may be a directly obtained fermentation stock solution, or may be a treatment liquid obtained from fermentation stock solution where impurity is removed, including, but not limited to, a fermentation broth where bacteria and pigment is removed. Further, the fermentation broth of pentanediamine salt may also be a concentrated solution of a fermentation stock solution or the treatment liquid after concentration. Any suitable methods in the prior art can be applied for impurity removal and concentration.

The pH of the enzyme converting solution or fermentation broth of pentanediamine salt obtained by industrial production is generally less than 9. Under this condition, pentanediamine is present in the form of salt. The pentanediamine salt has a high boiling point and low volatility and cannot be directly evaporated from an aqueous solution. To extract pentanediamine, it is generally necessary to liberate pentanediamine salt in the system for subsequent steps. Usually, a solution containing a pentanediamine salt, such as an enzyme converting solution of pentanediamine, is directly concentrated and evaporated after addition of sodium hydroxide. Due to the presence of high content of inorganic salt and large amount of impurities such as bacteria in the solution, less amount of pentanediamine is obtained in the final evaporation, and thus low yield is obtained. Also, inorganic salt precipitates after concentration, and large amount of residue is present after evaporation. The residue contains pentanediamine or pentanediamine salt and a large amount of soluble inorganic salts as well, and the waste is difficult to be handled.

In order to overcome the above drawbacks, a poorly soluble base such as calcium oxide, calcium hydroxide, magnesium hydroxide or the like is added in the extraction method of the present invention, and the poorly soluble inorganic salt thus produced can be easily removed by solid-liquid separation without remaining in the solution system, or the subsequent distillation/evaporation treatment can be directly carried out without filtration in advance. The inorganic salt precipitated out can effectively disperse the bacteria or other impurities in the system, thereby alleviating the influence on the distillation/evaporation process and obtaining an ideal extraction rate of pentanediamine.

The amount of the poorly soluble base such as calcium oxide, calcium hydroxide, magnesium hydroxide or the like can be easily determined by those skilled in the art to ideally make the reaction of sulfate, phosphate, carbonate of 1,5-pentanediamine in the solution system as complete as possible, and it can be appropriately increased based on the theoretical amount to ensure a complete reaction without leaving a large amount of residue. Moreover, it can be supplemented or reduced according to the actual reaction situation, which is not limited in the present invention.

In some preferred embodiments, the basic substance of the present invention may further comprise one or more of solid or liquid sodium hydroxide, potassium hydroxide, and ammonia. When the solution system contains anions in addition to sulfate, carbonate or phosphate, it is preferred to add an appropriate amount of a soluble strong base such as sodium hydroxide, potassium hydroxide or the like for reaction to give pentanediamine, and the amount thereof can be readily determined by those skilled the prior art, in order to ideally make the reaction of 1,5-pentanediamine salt in the solution system as complete as possible. Generally, the amount can be appropriately increased based on the theoretical amount to ensure a complete reaction without leaving a large amount of residue. Further, it can be supplemented or reduced according to the actual reaction situation, which is not limited in the present invention.

In some preferred embodiments, the basic substance comprises solid calcium oxide.

The purity of the basic substance as used in the present invention relates to the sources of the raw materials. Provided that the impurities do not contain components that can affect the quality of the pentanediamine product, any sources can be used in the present invention. In some embodiments, other substances that do not react with the pentanediamine salt may be contained in the basic substance. For example, calcium carbonate impurities in calcium oxide, being the impurities in the production process of calcium oxide, are present in industrial calcium oxide products, but they do not affect the reaction in the present invention.

In the present invention, the manner of adding the basic substance is not particularly limited. The basic substance may be added all at one time or batchwisely, or the components of the mixture of the basic substances may be separately charged, or the components are firstly mixed before added all at one time. Preferably, the strong basic substance such as sodium hydroxide or potassium hydroxide may be added as an aqueous solution having a concentration in percentage by mass of 10 to 60%. The basic substance to be added may be a single type or a mixture of two or more types; a strong basic substance such as sodium hydroxide or potassium hydroxide may be added together with a poorly soluble base, or a poorly soluble base may be added first, followed by addition of a strong basic substance to the reaction system before the subsequent treatment.

In general, the amount of the basic substance to be added can be determined based on the amount of the 1,5-pentanediamine salt in the solution. The basic substance may suitably exceed the required theoretical amount to ensure a complete reaction.

The solution system containing 1,5-pentanediamine salt may be originated from many sources, and that 1,5-pentanediamine salt may also contain a small amount of other components, such as hydrochloride, dicarboxylate. To this, the extraction method of the present invention still applies.

In one embodiment of the process according to the invention, the solution containing 1,5-pentanediamine salt further comprises, but not limited to, hydrochloride and/or dicarboxylate of 1,5-pentanediamine.

In some embodiments, when the solution system further contains other salt components such as hydrochloride, the basic substance contains both a poorly soluble basic substance and a strongly soluble basic substance. The poorly soluble basic substance such as calcium oxide or calcium hydroxide, magnesium hydroxide or the like may be added in an amount that at least ensure the complete precipitation of sulfate, phosphate, and carbonate, and may also be appropriately added in excess.

In one embodiment of the method according to the present invention, the temperature at which the basic substance is added to the solution system is not particularly limited, provided that the pentanediamine salt and the basic substance can sufficiently react. In general, the reaction rate of the pentanediamine salt with the basic substance is relatively higher at a higher temperature; the reaction rate of the pentanediamine salt with the basic substance is relatively lower at a lower temperature. In some embodiments, the temperature at which the basic substance is added may range from room temperature to 95° C. In some preferred embodiments, the temperature at which the basic substance is added is above 60° C., more preferably above 80° C. The reaction time after the addition of the basic substance to the solution system containing 1,5-pentanediamine salt is not particularly limited, provided that the pentamethylene salt can be sufficiently reacted with the basic substance, which can be adjusted according to actual situations. In some embodiments, the reaction time of the pentanediamine salt with the basic substance is longer than 1 hour, preferably longer than 1.5 hours.

After addition of a basic substance to a solution containing 1,5-pentanediamine salt, free 1,5-pentanediamine and other compounds are formed in the solution, such as an inorganic salt formed by the reaction, unreacted 1,5-pentanediamine salt, impurities such as bacteria or proteins or residual sugars which are not separated in the fermentation broth or enzyme converting solution of 1,5-pentanediamine. The inorganic salt may comprise calcium salt/magnesium salt precipitate and/or dissolved sodium salt/potassium salt, and the precipitate may, for example, be magnesium sulfate, calcium sulfate, magnesium carbonate, calcium carbonate, magnesium phosphate or calcium phosphate.

In one embodiment of the method according to the invention, the method further comprises subjecting the resulting solution system containing free 1,5-pentanediamine to distillation/evaporation to produce a solution of 1,5-pentanediamine. The solids contained in the solution system may be removed prior to distillation/evaporation, or the solution system may be directly subjected to distillation/evaporation without treatment. In the present invention, the step of "distillation/evaporation" means subjecting a solution system containing free 1,5-pentanediamine to heating to evaporate water and pentanediamine of relatively low boiling point therein, and then collecting the water vapor containing pentanediamine obtained from evaporation to provide an aqueous solution of 1,5-pentanediamine, of which the operational step is known or readily available to those skilled in the art.

In one embodiment of the method according to the invention, the method further comprises separating the solid substance in the solution system after forming a solution containing free 1,5-pentanediamine. The manner of separation is not limited in the present invention, and conventional solid-liquid separation methods such as plate and frame suction filtration, membrane filtration, and various forms of centrifugation can be employed. Since separation of the solid substances may take away a small amount of unreacted calcium oxide, calcium hydroxide, magnesium oxide and other basic substances, 1,5-pentanediamine salt should be reacted as complete as possible before separation, and also basic substances may be replenished in an appropriate amount after separation to avoid incomplete reaction of the pentanediamine salt, which affects the final yield of pentanediamine.

In the present invention, pentanediamine in the aqueous solution of pentanediamine obtained by distillation/evaporation can be separated from water to obtain a qualified pentanediamine product. A pure pentanediamine product may be obtained by subjecting the thus obtained 1,5-pentanediamine aqueous solution to a conventional aqueous solution treatment, including but not limited to distillation, and that the thus obtained 1,5-pentanediamine aqueous solution can also directly participate as a raw material in a downstream reaction such as a polymerization reaction. In some preferred embodiments of the invention, the solution may be concentrated prior to distillation/evaporation. Since the boiling point of water is lower than the boiling point of pentanediamine, the purpose of concentration is to undergo concentration by heating using a lower energy-efficiency heating medium to achieve energy saving, and to increase the concentration of the pentanediamine product obtained in the stage of distillation/evaporation. The manner of concentration and the concentration factor can be determined according to actual needs, which is not particularly limited in the present invention.

In one embodiment of the process according to the invention, the temperature of distillation/evaporation may be from 40 to 250° C., and pentanediamine and water may be distilled/evaporated in a slow temperature rising manner to form an aqueous solution of pentanediamine. The temperature of distillation/evaporation is preferably not less than 120° C., more preferably not less than 150° C.

In one embodiment of the process according to the invention, the distillation/evaporation is carried out under vacuum condition, such as at a pressure of not greater than −0.05 MPa, preferably not greater than −0.08 MPa, more preferably not greater than −0.09 MPa, and most preferably not greater than −0.095 MPa. The above pressure values are all gauge pressure values.

In some preferred embodiments of the invention, the temperature of the distillation/evaporation process is slowly increased from 70° C. to 180° C. and the distillation/evaporation pressure is −0.095 MPa.

Separation of pentanediamine by distillation/evaporation is carried out under the conditions of the process of the present invention, the recovery of pentanediamine is more effective. As the distillation/evaporation process proceeds, the excess base in the system further react with the residual pentanediamine salt to form more pentanediamine, and these amines can be efficiently evaporated to give a desired recovery rate of pentanediamine.

In one embodiment of the method according to the invention, the solution containing 1,5-pentanediamine salt may also be subjected to a pretreatment process such as sterilization, decolorization prior to the addition of the basic substance.

In one embodiment of the method according to the invention, the solution containing 1,5-pentanediamine salt may also be subjected to a pretreatment process such as sterilization, decolorization prior to separation of 1,5-pentanediamine.

In implementing the separation process of the present invention, the process actually employed may not be limited to those as mentioned above, and that raw materials and/or process steps may be simply or easily additionally added or modified by those skilled in the art, without causing any intrinsic changes to the main body of the separation process, and the main process is only complemented or improved in some aspects.

The invention will be described in detail with reference to the following examples, by which the features and advantages of the invention will be more apparent. It should be noted, however, that the invention is not limited to the embodiments as set forth herein.

All concentrations in the examples and comparative examples are concentrations in percentage by weight, and all pressures are gauge pressures, unless otherwise specified.

The purity of pentanediamine or its salt is determined by gas chromatography normalization. The method for detecting pentanediamine was carried out by NMR nuclear magnetic resonance spectrometry to detect the characteristic absorption peak of pentanediamine.

The concentration of pentanediamine as depicted in the following examples all refer to the mass concentration of pentanediamine.

EXAMPLE 1

To 600 g enzyme converting solution of pentanediamine sulfate containing bacteria, the mass concentration of pentanediamine was determined to be 3.9%. 22 g of calcium hydroxide powder (content: 90% or more) was added, the temperature was controlled below 95° C. The mixture was stirred for 90 minutes, filtered through a Buchner funnel and the filter cake was rinsed with 200 mL of water. The filtrates were all transferred to a 1 L flask. The mixed solution was evaporated on a rotary evaporator at a pressure of −0.095 MPa. The heating temperature of the oil bath was gradually increased to 180° C. 765 g of an aqueous solution containing 2.9% of pentanediamine was obtained. The yield of pentanediamine was 94.8%, and a trace amount of precipitate remained on the bottom of the flask.

EXAMPLE 2

To 600 g enzyme converting solution of pentaneamine salt (phosphate accounted for 89% of the total molar amount of anions; chloride ion was 11%), and the mass concentration of pentanediamine was determined to be 3.58%. 18 g of calcium hydroxide powder (content: 90% or more) was added, the temperature was controlled at 60° C. The mixture was stirred for 60 minutes, filtered through a Buchner funnel and the filter cake was rinsed with 200 ml of deionized water. All filtrates were combined and transferred to a 1 L flask. 3 g of solid potassium hydroxide and 20 g of glass beads was added to the filtrate. The mixture was heated, and the pressure was gradually reduced to −0.095 MPa for evaporation. The heating temperature of the oil bath was gradually increased to 180° C. 766 g of an aqueous solution containing 2.67% of pentanediamine was obtained. The yield of pentanediamine was 95.2%, and a trace amount of solid precipitate was remained on the bottom of the flask.

EXAMPLE 3

To 600 g fermentation broth of pentanediamine carbonate, the mass concentration of pentanediamine was determined to be 2.0%. Evaporation was carried out on a rotary evaporator at a pressure of −0.095 MPa, the temperature of the water bath was controlled at 90° C. Concentration was carried out until 100 g of residue was left, followed by addition of 10 g of magnesium hydroxide powder, the temperature was controlled at 80° C. and stirring was kept for 90 minutes. The mixture was filtered through a Buchner funnel, solid layer was rinsed with 300 g of purified water, the resulting filtrates were then combined, the combined filtrate was evaporated on a rotary evaporator at a pressure of −0.095 MPa, the heating temperature of the oil bath was gradually increased from 70° C. to 180° C., and distillation was carried out until basically no more liquid was distilled out. The evaporation liquid was combined to give 377 g of an aqueous solution containing 2.95% of pentanediamine. The yield of pentanediamine was 92.6%, and a trace amount of precipitate was remained on the bottom of the flask.

EXAMPLE 4

To 600 g concentrated enzyme converting solution of pentanediamine sulphate containing bacteria, the mass concentration of pentanediamine was determined to be 15.1%. 80 g of calcium hydroxide powder (content: 90% or more) was added, and the temperature was controlled at 95° C., and the mixture was stirred for 120 minutes. 100 g of glass beads were added to the mixed solution to enhance stirring, and the mixture was evaporated on a rotary evaporator at a pressure of −0.095 MPa, and the heating temperature of the oil bath was gradually increased to 180° C. 521 g of an aqueous solution containing 16.7% of pentanediamine was obtained. The yield of pentanediamine was 96.0%, and a loose solid precipitate was remained on the bottom of the flask, viscous substance was not found.

EXAMPLE 5

To 600 g concentrated enzyme converting solution of pentadiamine salt (prepared from lysine sulfate), the mass concentration of pentanediamine was determined to be 15.1%. 60 g of calcium oxide powder (content: 95% or more) was added, the temperature was controlled at 75° C., and the mixture was stirred for 120 minutes, filtered through a Buchner funnel and the filter cake was rinsed with 500 mL deionized water at twice. All filtrates were combined and then evaporated. The mixed solution was evaporated on a rotary evaporator at a pressure of −0.095 MPa. The heating temperature of the oil bath was gradually increased from 70° C. to 180° C. 942 g of an aqueous solution containing 9.14% of pentanediamine was obtained. The yield of pentanediamine was 95.0%, and a small amount of precipitate was remained on the bottom of the flask.

EXAMPLE 6

To 100 kg concentrated enzyme converting solution of pentanediamine sulphate containing bacteria, the concentration of pentanediamine is determined to be 15.1%. 11 kg of calcium oxide powder (content: 95% or more) was added, the temperature was controlled at 85 to 95° C., stirring was kept for 180 minutes, followed by centrifugation in an industrial centrifuge to give a centrifugate. The obtained solid was washed with 100 kg of deionized water at twice and centrifuged with an industrial centrifuge to obtain 159 kg in total of the centrifugal supernatant. The obtained centrifugal supernatant was evaporated in an evaporation vessel at a pressure of −0.095 MPa. Most of the water was first distilled off, and then the heating temperature was gradually increased from 70° C. to 180° C. until no more gas was distilled off. All evaporates were combined to give 147 kg of an aqueous solution containing 9.6% of pentanediamine. The evaporation yield of pentanediamine is 93.5%, and a small amount of residue of good fluidity was left on the bottom of the evaporation vessel, which was discharged while hot when the pressure was liberated to atmospheric pressure.

EXAMPLE 7

To 1000 kg concentrated enzyme converting solution of 1,5-pentanediamine sulfate containing lysine decarboxylase cells, the concentration of 1,5-pentanediamine was determined to be 15.1%. 110 kg of calcium oxide powder (content: more than 95%) was added, the temperature was controlled at about 90° C., sufficient stirring was ensured for 180 minutes. Then, the obtained mixed solution system was gradually transferred to a paddle vacuum dryer (KJG/110) (at 20 rpm) for evaporation under heating. The vacuum degree was controlled to −0.09 to −0.08 Mpa, the temperature of the heat transfer oil was 200° C., and the condensate of the evaporated gas was collected. 827 kg of an aqueous solution containing 17.4% of 1,5-pentanediamine was obtained. The yield of 1,5-pentanediamine was 95.6%, and loose solid powder was remained in the paddle vacuum dryer, agglomeration and deposition on wall was not found.

COMPARATIVE EXAMPLE

To 600 g concentrated enzyme converting solution of pentanediamine sulphate containing bacteria, the mass concentration of pentanediamine was determined to be 15.1%. 76 g of sodium hydroxide powder (chemically pure) was slowly added while stirring, and the temperature was controlled below 60° C., stirring was kept for 120 minutes. 100 g of glass beads were added to the mixed solution to enhance stirring, and the mixture was evaporated on a rotary evaporator at a pressure of −0.095 MPa, and the heating temperature of the oil bath was gradually increased to 180° C. 515 g of an aqueous solution containing 11.3% of pentanediamine was obtained. The yield of pentanediamine is 64.2%. Viscous precipitate was found at the bottom of the eggplant-shaped flask, which has poor fluidity and was unable to pour out of the flask by itself when the pressure was liberated to atmospheric pressure. At room temperature, the bottom residue was found to be agglomerated and deposited on wall.

It can be seen from the examples and the comparative examples that the method of the present invention can obtain the desired extraction rate of pentanediamine without generating refractory distillation/evaporation wastes. Further, the use of solid basic substances of calcium/magnesium can greatly lower the cost of raw materials, and is convenient for storage and transportation. The reaction and distillation/evaporation process allow the presence of solid precipitates, and thus solid-liquid separation is not designed, by which production efficiency can be greatly improved, and production cost can be reduced as well. More importantly, since large amount of soluble wastes of salts is avoided from generation, soluble salts are prevented from entering into the wastewater, thereby the difficulty of wastewater treatment as well as the cost of wastewater treatment can be greatly lowered, which is also environmentally friendly.

Although the preferable embodiments of the present invention has been described and illustrated in detail, it is clearly understood that the same is not to be taken by way of limitation, it should be understood that various changes, substitutions, and alterations could be made hereto by an ordinary skilled person in the art without departing from the spirit and scope of the invention as defined by the appended claims.

What is claimed is:

1. A method for extracting 1, 5-pentanediamine from a solution system containing a 1,5-pentanediamine salt, comprising:
   (i) adding to the solution system a basic substance to form a resulting solution system containing free 1,5-pentanediamine, the 1,5-pentanediamine salt being selected from a group consisting of sulfate, carbonate, phosphate, hydrochloride, and dicarboxylate of 1,5-pentanediamine, and the basic substance being selected from a group consisting of solid magnesium hydroxide, calcium oxide, and magnesium oxide; and
   (ii) directly subjecting the resulting solution system containing free 1,5-pentanediamine to distillation/evaporation to obtain a solution of 1,5-pentanediamine, without separating solid substances from the resulting solution system or adding organic solvent prior to distillation/evaporation.

2. The method according to claim 1, wherein the molar amount of sulfate, carbonate, and phosphate of 1,5-pentanediamine in the solution system is not less than 70% of the total molar amount of the 1,5-pentanediamine salt in the solution system.

3. The method according to claim 1, wherein the solution system containing the 1,5-pentanediamine salt is an aqueous solution containing the 1,5-pentanediamine salt, an enzyme converting solution of 1,5-pentanediamine or a fermentation broth of 1,5-pentanediamine.

4. The method according to claim 2, wherein the solution system containing the 1,5-pentanediamine salt is an aqueous solution containing the 1,5-pentanediamine salt, an enzyme converting solution of 1,5-pentanediamine or a fermentation broth of 1,5-pentanediamine.

5. The method according to claim 1, wherein the basic substance is added at a temperature from 60° C. to 95° C.

6. The method according to claim 2, wherein the basic substance is added at a temperature from 60° C. to 95° C.

7. The method according to claim 1, further comprising concentrating the resulting solution system containing free 1,5-pentanediamine prior to distillation/evaporation.

8. The method according to claim 1, wherein the step of distillation/evaporation is performed at a temperature from 40 to 250° C.

9. The method according to claim 1, wherein the step of distillation/evaporation is performed at a pressure not higher than −0.05 Mpa, the pressure value being a gauge pressure value.

10. The method according to claim 1, further comprising subjecting the solution system to a pretreatment process prior to adding the basic substance, wherein the pretreatment process is selected from the group consisting of a sterilization process, a decolorization process, a concentration process, and a combination thereof.

11. The method according to claim 1, wherein the molar amount of sulfate, carbonate, and phosphate of 1, 5-pentanediamine in the solution system is not less than 75% of the total molar amount of the 1,5-pentanediamine salt in the solution system.

12. The method according to claim 1, wherein the molar amount of sulfate, carbonate, and phosphate of 1, 5-pentanediamine in the solution system is not less than 80% of the total molar amount of the 1,5-pentanediamine salt in the solution system.

13. The method according to claim 1, wherein the molar amount of sulfate, carbonate, and phosphate of 1,5-pentanediamine in the solution system is not less than 85% of the total molar amount of the 1,5-pentanediamine salt in the solution system.

* * * * *